US00PP34441P2

(12) United States Plant Patent
Stewart et al.

(10) Patent No.: US PP34,441 P2
(45) Date of Patent: Jul. 26, 2022

(54) STRAWBERRY PLANT NAMED 'DRISSTRAWNINETYONE'

(50) Latin Name: ***Fragaria* x *ananassa***
Varietal Denomination: DrisStrawNinetyOne

(71) Applicant: Driscoll's, Inc., Watsonville, CA (US)

(72) Inventors: Philip J. Stewart, Watsonville, CA (US); Agustin Renteria, Watsonville, CA (US); Amy M. Edmondson, Watsonville, CA (US); Iana Kostina, Watsonville, CA (US); Debora Liabeuf, Watsonville, CA (US); Kevin Coons, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 17/307,935

(22) Filed: May 4, 2021

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209
CPC ..... A01H 6/7409
See application file for complete search history.

(56) References Cited

U.S. PATENT DOCUMENTS

PP1,745 P 8/1958 Lang
PP3,981 P 11/1976 Bringhurst et al.
PP4,487 P 11/1979 Bringhurst et al.
PP4,538 P 5/1980 Bringhurst et al.
PP5,262 P 7/1984 Voth et al.
PP5,265 P 7/1984 Voth et al.
PP5,266 P 7/1984 Bringhurst et al.
PP5,300 P 10/1984 Johnson, Jr. et al.
PP5,840 P 12/1986 Johnson, Jr. et al.
PP6,191 P 5/1988 Johnson, Jr. et al.
PP6,231 P 7/1988 Johnson, Jr. et al.
PP6,578 P 1/1989 Voth et al.
PP6,579 P 1/1989 Bringhurst et al.
PP7,024 P 9/1989 Johnson, Jr. et al.
PP7,172 P 2/1990 Voth et al.
PP7,522 P 5/1991 Johnson, Jr. et al.
PP7,614 P 8/1991 Bringhurst et al.
PP7,615 P 8/1991 Bringhurst et al.
PP8,086 P 1/1993 Nelson et al.
PP8,205 P 4/1993 Nelson et al.
PP8,649 P 3/1994 Sjulin et al.
PP8,661 P 3/1994 Bringhurst et al.
PP8,708 P 5/1994 Voth et al.
PP8,745 P 5/1994 Sjulin et al.
PP9,130 P 5/1995 Sjulin et al.
PP9,909 P 6/1997 Ackerman et al.
PP10,221 P 2/1998 Sjulin et al.
PP10,534 P 8/1998 Sjulin et al.
PP10,642 P 10/1998 Amorao et al.
PP11,035 P 8/1999 Mowrey et al.
PP11,277 P 3/2000 Gilford et al.
PP11,279 P 3/2000 Gilford et al.
PP11,522 P 9/2000 Amorao et al.
PP11,548 P 10/2000 Amorao et al.
PP11,554 P 10/2000 Sjulin et al.
PP11,639 P 11/2000 Mowrey et al.
PP12,186 P2 11/2001 Gilford et al.
PP12,436 P2 3/2002 Amorao et al.
PP12,577 P2 4/2002 Amorao et al.
PP12,817 P2 7/2002 Gilford et al.
PP12,899 P2 9/2002 Mowrey et al.
PP13,386 P2 12/2002 Mowrey et al.
PP13,469 P3 1/2003 Larson et al.
PP14,005 P3 7/2003 Amorao et al.
PP14,062 P3 8/2003 Amorao et al.
PP14,109 P3 8/2003 Gilford et al.
PP14,771 P3 5/2004 Amorao et al.
PP15,145 P2 9/2004 Mowrey et al.
PP15,308 P2 11/2004 Sjulin et al.
PP15,375 P2 11/2004 Mowrey et al.
PP15,435 P2 12/2004 Sjulin et al.
PP15,596 P2 3/2005 Amorao et al.
PP15,731 P2 4/2005 Amorao et al.
PP15,752 P2 5/2005 Gilford et al.
PP16,070 P2 10/2005 Gilford et al.
PP16,238 P2 2/2006 Amorao et al.
PP16,241 P2 2/2006 Mowrey et al.
PP16,298 P2 2/2006 Gilford et al.
PP16,299 P2 2/2006 Gilford et al.
PP16,475 P2 4/2006 Gilford et al.
PP16,558 P3 5/2006 Lopez
PP18,000 P2 9/2007 Meulenbroek
PP18,040 P3 9/2007 Mowrey et al.
PP18,041 P3 9/2007 Gilford
PP18,458 P2 1/2008 Ferguson et al.
PP18,575 P3 3/2008 Amorao et al.
PP18,878 P2 6/2008 Mowrey et al.
PP19,240 P2 9/2008 Gilford et al.
PP19,673 P3 2/2009 Ferguson et al.
PP19,767 P2 2/2009 Shaw et al.
PP20,248 P3 9/2009 Rogers et al.
PP20,363 P2 9/2009 Chandler
PP20,701 P2 2/2010 Gilford et al.
PP20,731 P2 2/2010 Mowrey et al.
PP20,733 P2 2/2010 Mowrey et al.
PP20,735 P2 2/2010 Ferguson
PP20,775 P2 2/2010 Mowrey et al.
PP20,922 P2 4/2010 Gilford et al.
PP21,538 P2 11/2010 Gilford et al.
PP21,559 P2 12/2010 Ferguson et al.
PP21,762 P2 3/2011 Stewart et al.
PP22,040 P3 7/2011 Stewart et al.

(Continued)

*Primary Examiner* — Anne Marie Grunberg

(74) *Attorney, Agent, or Firm* — Morrison & Foerstser LLP

(57) ABSTRACT

A new and distinct variety of strawberry plant named 'DrisStrawNinetyOne', particularly selected for the shelf life, firmness, and large size of the fruit, as well as its good performance in organic settings, is disclosed.

6 Drawing Sheets

(56) References Cited

U.S. PATENT DOCUMENTS

| | | | |
|---|---|---|---|
| PP22,218 | P2 | 11/2011 | Ferguson et al. |
| PP22,247 | P2 | 11/2011 | Ferguson |
| PP23,107 | P2 | 10/2012 | Ferguson et al. |
| PP23,148 | P2 | 10/2012 | Gilford et al. |
| PP23,377 | P2 | 2/2013 | Ferguson et al. |
| PP23,378 | P2 | 2/2013 | Pullen et al. |
| PP23,382 | P2 | 2/2013 | Ferguson et al. |
| PP23,383 | P2 | 2/2013 | Ferguson et al. |
| PP23,400 | P2 | 2/2013 | Ferguson et al. |
| PP23,401 | P2 | 2/2013 | Pullen et al. |
| PP23,459 | P2 | 3/2013 | Stewart et al. |
| PP23,506 | P3 | 4/2013 | Ferguson et al. |
| PP23,517 | P3 | 4/2013 | Ferguson et al. |
| PP24,096 | P3 | 12/2013 | Fear et al. |
| PP24,317 | P3 | 3/2014 | Ferguson et al. |
| PP24,333 | P3 | 3/2014 | Vitten et al. |
| PP24,395 | P3 | 4/2014 | Vitten et al. |
| PP24,533 | P3 | 6/2014 | Ferguson et al. |
| PP24,745 | P2 | 8/2014 | Vitten et al. |
| PP25,408 | P3 | 4/2015 | Vitten et al. |
| PP25,437 | P3 | 4/2015 | Vitten et al. |
| PP25,698 | P3 | 7/2015 | Ferguson et al. |
| PP25,699 | P3 | 7/2015 | Stewart et al. |
| PP25,747 | P3 | 7/2015 | Kibbe et al. |
| PP25,866 | P3 | 9/2015 | Ferguson et al. |
| PP26,800 | P3 | 6/2016 | Stewart et al. |
| PP26,801 | P3 | 6/2016 | Stewart et al. |
| PP26,802 | P3 | 6/2016 | Rodriguez Alcazar et al. |
| PP27,442 | P2 | 12/2016 | Kibbe et al. |
| PP27,645 | P3 | 2/2017 | Vitten et al. |
| PP27,682 | P3 | 2/2017 | Kibbe et al. |
| PP27,711 | P3 | 2/2017 | Vitten et al. |
| PP27,813 | P3 | 3/2017 | Ferguson et al. |
| PP29,289 | P3 | 5/2018 | Vitten et al. |
| PP29,728 | P2 | 10/2018 | Stewart et al. |
| PP29,729 | P2 | 10/2018 | Kibbe et al. |
| PP29,730 | P2 | 10/2018 | Kibbe et al. |
| PP29,731 | P2 | 10/2018 | Ferguson et al. |
| PP29,747 | P2 | 10/2018 | Vitten et al. |
| PP29,748 | P2 | 10/2018 | Vitten et al. |
| PP29,749 | P2 | 10/2018 | Stewart et al. |
| PP30,775 | P2 | 8/2019 | Carrillo Mendoza et al. |
| PP30,789 | P2 | 8/2019 | Ferguson et al. |
| PP30,818 | P2 | 8/2019 | Pakozdi et al. |
| PP30,851 | P2 | 8/2019 | Fear et al. |
| PP30,936 | P2 | 10/2019 | Stewart et al. |
| PP31,083 | P2 | 11/2019 | Carrillo Mendoza et al. |
| PP31,233 | P2 | 12/2019 | Pakozdi et al. |
| PP31,527 | P3 | 3/2020 | Carrillo Mendoza et al. |
| PP31,655 | P2 | 4/2020 | Carrillo Mendoza et al. |
| PP31,703 | P2 | 4/2020 | Stewart et al. |
| PP31,827 | P2 | 6/2020 | Ferguson et al. |
| PP31,896 | P2 | 6/2020 | Pakozdi et al. |
| PP31,935 | P2 | 7/2020 | Pakozdi et al. |
| PP32,079 | P2 | 8/2020 | Carrillo Mendoza et al. |
| PP32,080 | P2 | 8/2020 | Ferguson et al. |
| PP32,271 | P2 | 10/2020 | Ferguson et al. |
| PP32,305 | P3 | 10/2020 | Pakozdi et al. |
| PP32,498 | P2 | 11/2020 | Carrillo Mendoza et al. |
| PP32,499 | P3 | 11/2020 | Jacobs et al. |
| PP32,500 | P3 | 11/2020 | Stewart et al. |
| PP32,801 | P2 | 2/2021 | Ferguson et al. |
| PP32,814 | P2 | 2/2021 | Stewart et al. |
| PP32,824 | P2 | 2/2021 | Stewart et al. |
| PP33,070 | P2 | 5/2021 | Mendoza et al. |
| PP33,090 | P2 | 5/2021 | Mendoza et al. |
| 2003/0079263 | P1 | 4/2003 | Gilford et al. |
| 2013/0276182 | P1 | 10/2013 | Fear et al. |

STRAWBERRY PLANT NAMED 'DRISSTRAWNINETYONE'

Latin name:

Botanical classification: *Fragaria* x *ananassa.*

Varietal denomination: The varietal denomination of the claimed variety of strawberry plant is 'DrisStrawNinetyOne'.

BACKGROUND OF THE INVENTION

Cultivated strawberry is a hybrid species of the genus *Fragaria* that is grown worldwide for its fruit. Modern strawberry was first bred in Brittany, France, in the 18$^{th}$ century by crossing *Fragaria virginiana* with *Fragaria chiloensis*. Strawberry fruit is an aggregate accessory fruit, with the fleshy part of the fruit being derived from the receptacle that holds the ovaries.

Strawberry varieties vary widely in color, size, shape, flavor, season of ripening, degree of fertility, and susceptibility to disease. Certain varieties vary in foliage, and some vary in the relative development of their reproductive organs. Typically, strawberry flowers appear hermaphroditic in structure, but function as either male or female. Generally, commercial production of strawberry plants involves propagation from runners and distribution as either plugs or bare root plants. Cultivation is either perennial or annual plasticulture. During the off season, strawberries can also be produced in greenhouses.

Strawberry fruit is widely appreciated for its characteristic bright red color, aroma, juicy texture, and sweetness. Strawberry fruit is a popular fruit that is generally consumed either fresh or in prepared foods, such as preserves and baked goods.

Strawberry is an important and valuable fruit crop. Accordingly, there is a need for new varieties of strawberry plants. In particular, there is a need for improved varieties of strawberry plant that are stable, high yielding, and agronomically sound.

SUMMARY OF THE INVENTION

In order to meet these needs, the present invention is directed to an improved variety of strawberry plant. In particular, the invention relates to a new and distinct variety of strawberry plant (*Fragaria* x *ananassa*), which has been denominated as 'DrisStrawNinetyOne'.

Strawberry plant variety 'DrisStrawNinetyOne' originated from a cross between the proprietary female parent strawberry plant '131U152' (unpatented) and the proprietary male parent strawberry plant '140U203' (unpatented). Progeny plants from this cross, including 'DrisStrawNinetyOne', were asexually propagated via stolons in Shasta County, Calif. in the summer of 2014. Strawberry plant variety 'DrisStrawNinetyOne' was later specifically identified and selected in Monterey County, Calif. in May of 2015.

'DrisStrawNinetyOne' was subsequently asexually propagated via stolons, and has undergone testing in test plots in Monterey County, Calif. and Santa Barbara County, Calif. for four years (2016 to 2020). The present variety has been found to be stable and reproduce true to type through successive asexual propagations via stolons and tissue culture.

'DrisStrawNinetyOne' was particularly selected for the shelf life, firmness, and large size of the fruit, as well as its good performance in organic settings.

DESCRIPTION OF THE DRAWINGS

This new strawberry plant is illustrated by the accompanying photographs. The colors shown are as true as can be reasonably obtained by conventional photographic procedures. Unless indicated otherwise, the photographs are of plants that are 11-20 months old.

DETAILED BOTANICAL DESCRIPTION

Figure 1:
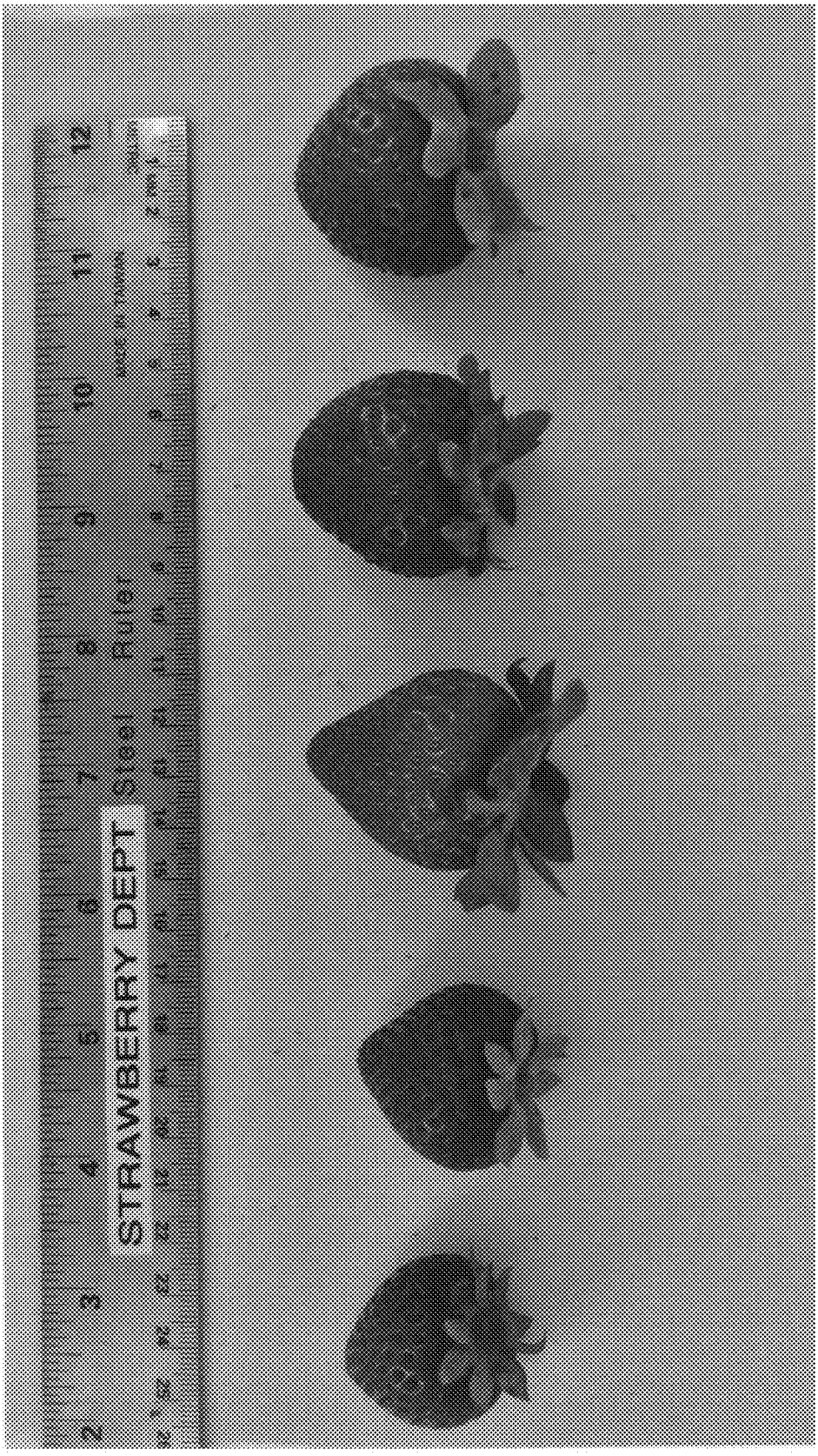
FIG. 1 illustrates whole fruit of variety 'DrisStrawNinetyOne'.
Figure 2:
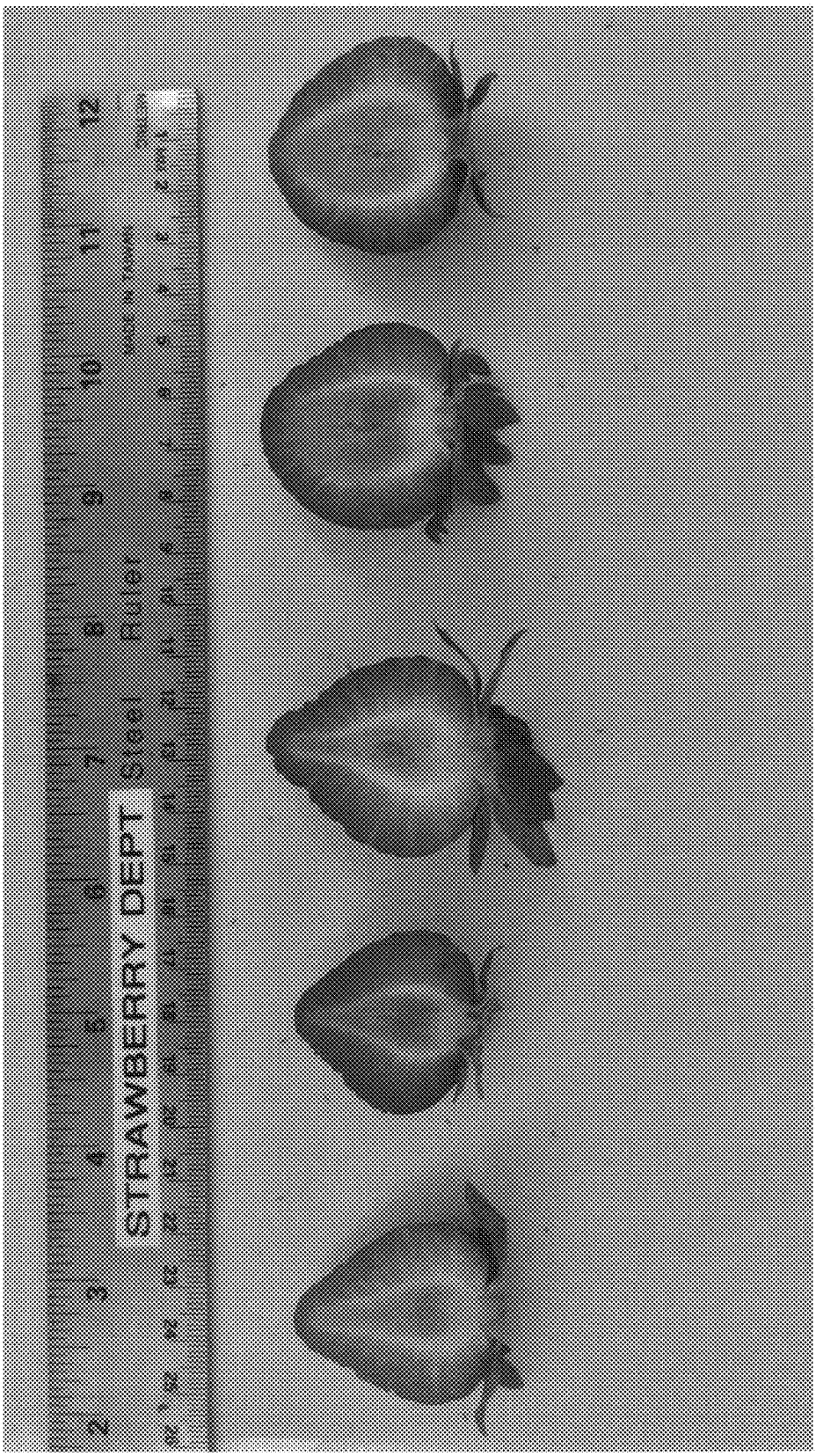
FIG. 2 illustrates longitudinal sections of fruit of variety 'DrisStrawNinetyOne'.
Figure 3:
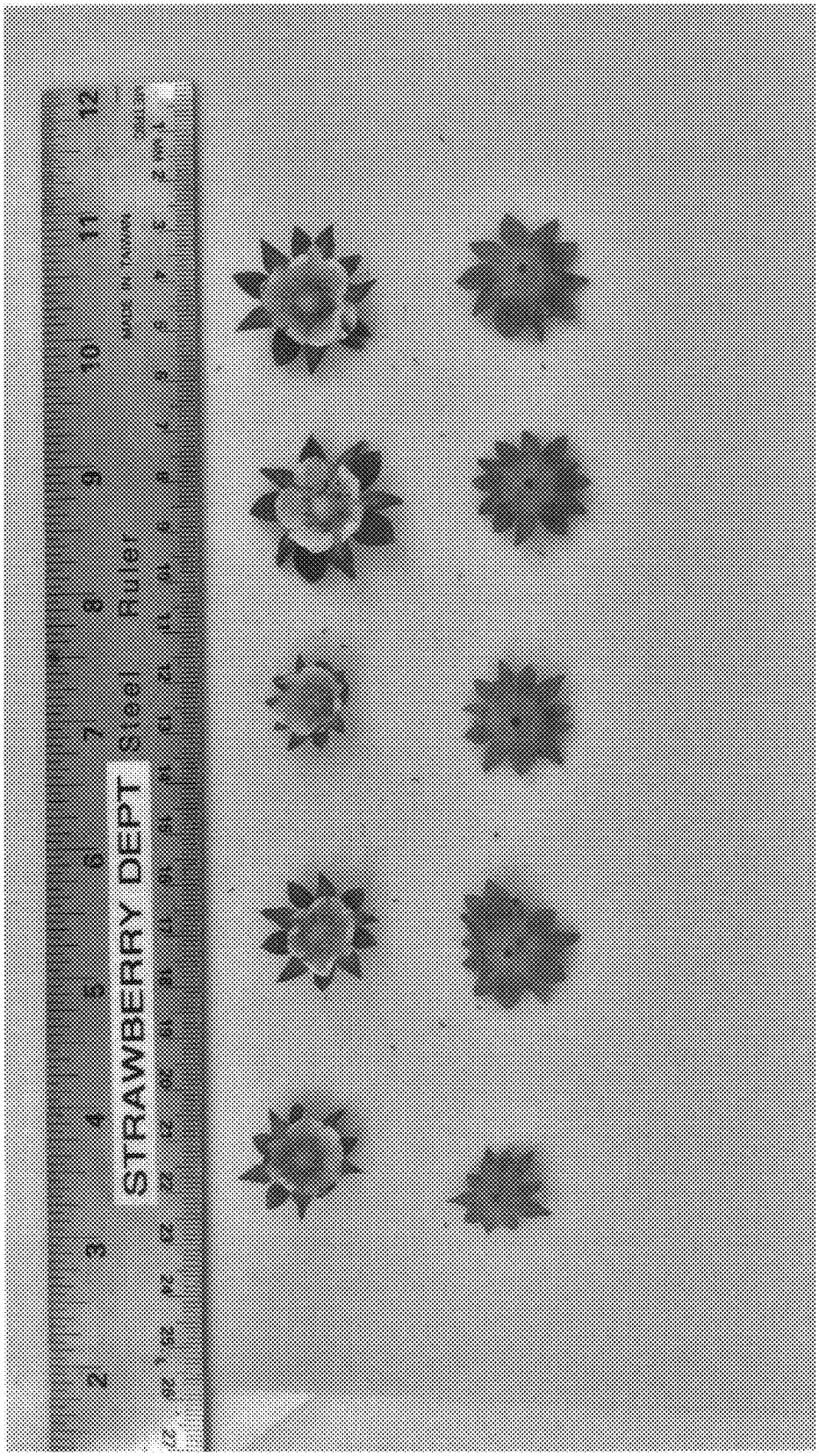
FIG. 3 illustrates flowers of variety 'DrisStrawNinetyOne'.
Figure 4:
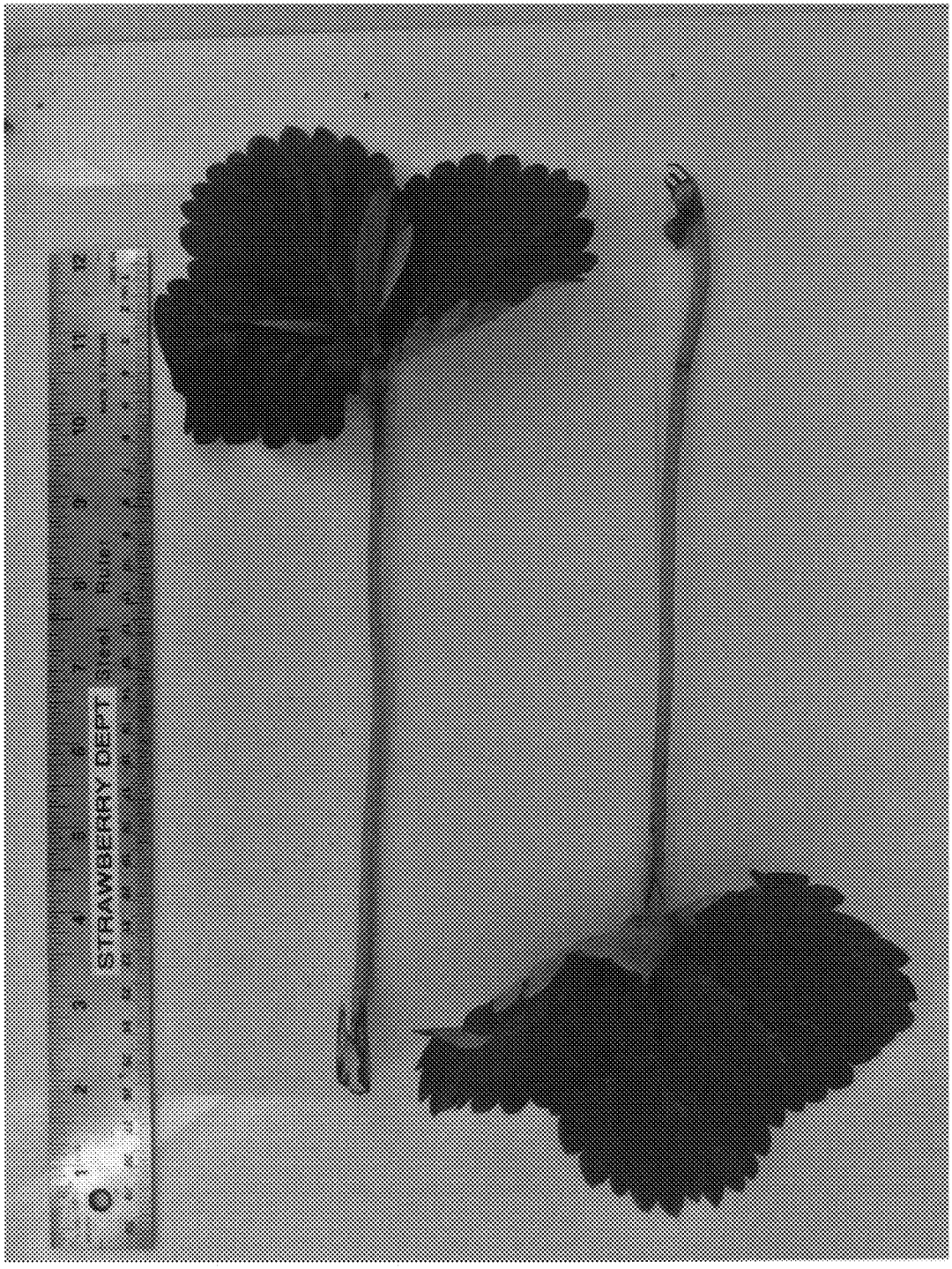
FIG. 4 illustrates leaves of variety 'DrisStrawNinetyOne'.
Figure 5:
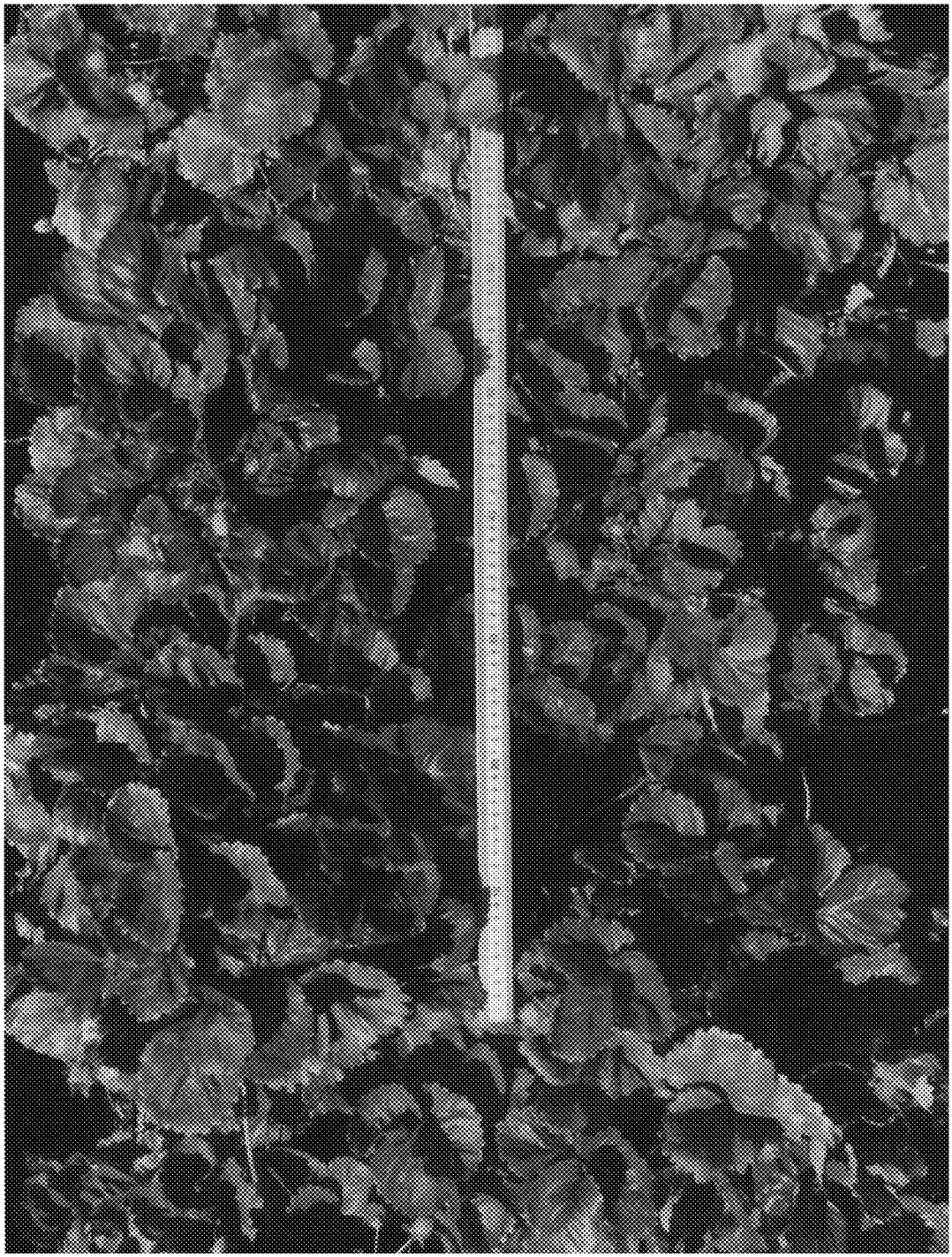
FIG. 5 illustrates whole plants of variety 'DrisStrawNinetyOne'.
Figure 6:
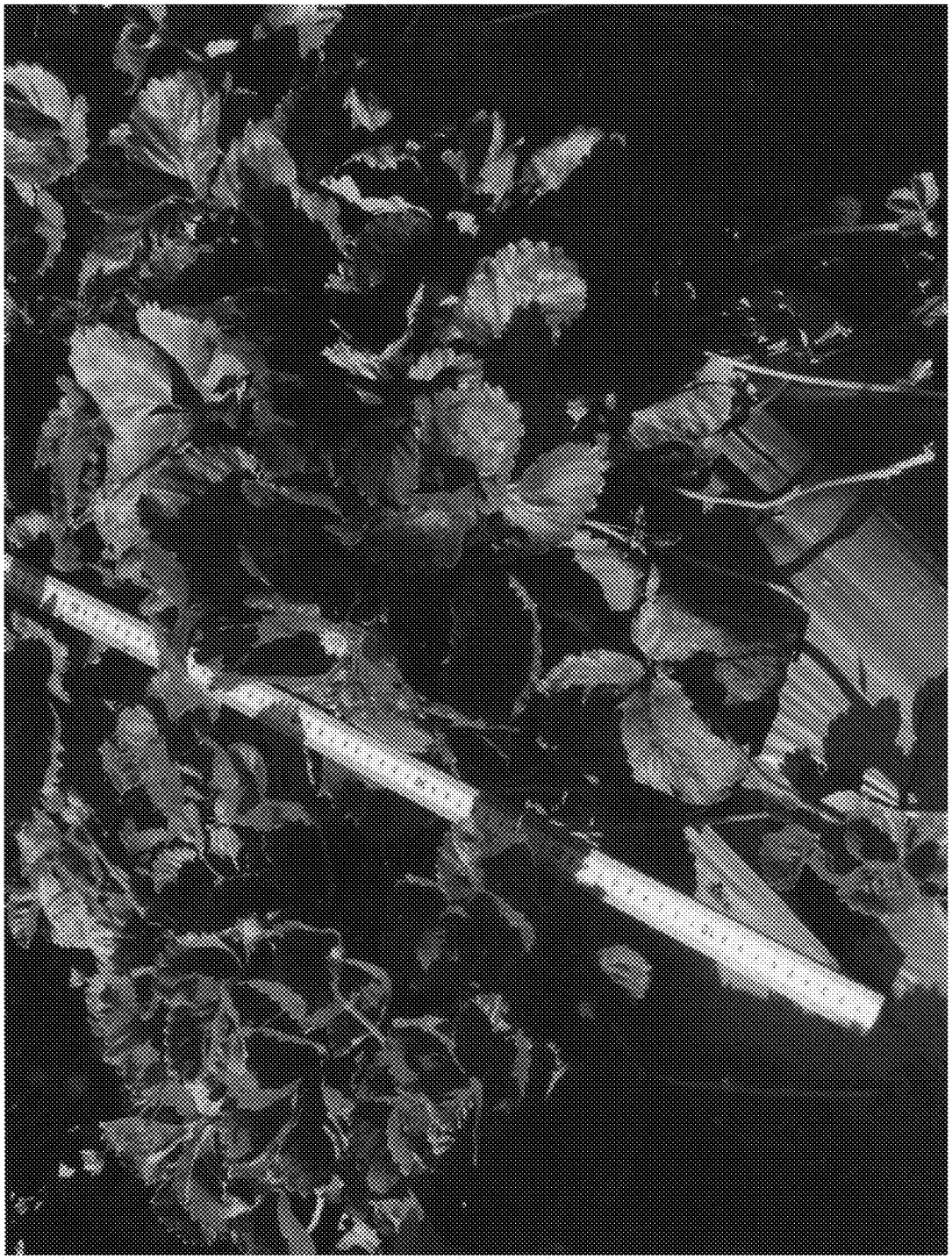
FIG. 6 illustrates another view of whole plants of variety 'DrisStrawNinetyOne'.

The following detailed descriptions set forth the distinctive characteristics of 'DrisStrawNinetyOne'. Unless indicated otherwise, the data which define these characteristics are based on observations taken from plants that were 11-20 months old grown in Monterey Count, Calif. and Santa Barbara County, Calif. from 2016 to 2020. This description is in accordance with UPOV terminology. Color designations, color descriptions, and other phenotypical descriptions may deviate from the stated values and descriptions depending upon variation in environmental, seasonal, climatic, and cultural conditions. 'DrisStrawNinetyOne' has not been observed under all possible environmental conditions. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Species.*—*Fragaria* x *ananassa.*

*Common name.*—Strawberry.

*Denomination.*—'DrisStrawNinetyOne'.

Parentage:

*Female parent.*—Proprietary strawberry plant '131U152' (unpatented).

*Male parent.*—Proprietary strawberry plant '140U203' (unpatented).

Plant:

*Height.*—25.7 cm.

*Diameter.*—43.1 cm.

*Number of crowns per plant.*—5.2.

*Growth habit.*—Semi-upright.

*Density of foliage.*—Dense.

*Vigor.*—Strong.

Stolon:

*Diameter at bract.*—3.1 mm.

*Anthocyanin coloration.*—Weak.

*Stolon color with anthocyanin present.*—RHS 145A (Strong yellow-green).

*Density of pubescence.*—Sparse.

*Number of stolons per plant.*—2.

Leaf:

*Number of leaflets.*—Three only.

*Color of upper leaf surface.*—RHS 139A (Dark yellowish green).

*Color of lower leaf surface*.—RHS 139C (Moderate yellow green).
*Blistering*.—Medium.
*Glossiness*.—Medium.
*Variegation*.—Absent.
*Terminal leaflet*.—Length: 7.4 cm. Width: 7.0 cm. Length/width ratio: 1.1. Number of teeth per terminal leaflet: 19.4. Shape of terminal leaflet base: Rounded. Margin: Serrate to crenate. Shape in cross section: Concave.
*Petiole*.—Color: RHS 144C (Strong yellow green). Length: 20.5 cm. Diameter: 3.9 mm. Attitude of hairs: Slightly outwards. Bract frequency (number present on each petiole): 0.
*Petiolule*.—Length: 11.1 mm. Diameter: 2.3 mm.
*Stipule*.—Length: 22 mm. Width: 11.9 mm. Anthocyanin coloration: Medium. Stipule color with anthocyanin present: RHS 163A (Deep orange yellow).

Inflorescence:
*Position of inflorescence in relation to foliage*.—Above.
*Pedicel*.—Attitude of hairs: Horizontal.
*Flower*.—Flower diameter (petal tip to petal tip on non-flattened flower): 15.5 mm. Arrangement of petals: Free. Size of calyx in relation to corolla: Larger. Stamen: Present. Number of flowers per flowering truss: 14.3.
*Petal*.—Length: 6.4 mm. Width: 8.2 mm. Length/width ratio: 0.8. Number of petals per flower: 5.3. Color of petal upper side: RHS 155A (Yellowish White). Color of petal lower side: RHS 155C (Greenish White).
*Pollen*.—Color: RHS 12A (Vivid yellow). Shape: Rounded tetrahedron.
*Stigma*.—Color: RHS 2B (Brilliant greenish yellow).
*Stamen*.—Number per flower: 24.
*Calyx*.—Color: RHS 139A (Dark yellowish green). Diameter (sepal tip to sepal tip, measured on back of flower): 24.6 mm.
*Sepal*.—Color: RHS 139A (Dark yellowish green). Length: 8.9 mm. Width: 4.8 mm. Number of sepals per flower: 10.4.
*Flowering*.—Flowering interval: February to November (in Watsonville, Calif.).

Fruit:
*Fruit size*.—Length: 37.9 mm. Width: 33.9 mm. Length/width ratio: 1.1.
*Fruit hollow*.—Length: 8.5 mm. Width: 2.9 mm. Length/width ratio: 2.9.
*Shape*.—Conical.
*Difference in shape of terminal and other fruits*.—None or very slight.
*Fruit color*.—RHS 46A (Strong red).
*Evenness of color*.—Even or very slightly uneven.
*Glossiness*.—Medium.
*Evenness of surface*.—Even or very slightly uneven.
*Width of band without achenes*.—Narrow.
*Position of achenes*.—Level with surface.
*Achene color*.—RHS 42B (Strong reddish orange).
*Number of achenes per fruit*.—363.
*Position of calyx attachment*.—Level with fruit.
*Attitude of sepals*.—Outwards.
*Diameter of calyx in relation to diameter of fruit*.—Slightly larger.
*Adherence of calyx*.—Strong.
*Color of flesh* (*excluding core*).—RHS 43A (Vivid reddish orange).
*Color of core*.—RHS 43B (Vivid reddish orange).
*Soluble solids* (*in ° Brix*).—7.3.
*Fruiting*.—Harvest interval: March to November (in Watsonville, Calif.). Type of bearing: Partially remontant. Productivity: 1.9 kg to 2.7 kg of fruit per plant per season from 11- to 20-month-old plants when grown in Watsonville, Calif.

Resistance to abiotic stress, pests, and diseases:
*Powdery mildew* (*Podosphaera macularis*).—Moderately susceptible.

COMPARISON WITH PARENTAL AND REFERENCE VARIETIES

'DrisStrawNinetyOne' differs from the female parent proprietary strawberry plant '131U152' (unpatented) in that 'DrisStrawNinetyOne' produces fruit that are firmer, have longer shelf life, better flavor, and lower in yield when compared to '131U152'.

'DrisStrawNinetyOne' differs from the male parent proprietary strawberry plant '140U203' (unpatented) in that 'DrisStrawNinetyOne' produces fruit that are larger in size, higher in yield, and less sweet in taste when compared to '140U203'.

'DrisStrawNinetyOne' differs from the reference variety 'DrisStrawFortyFour' (U.S. Plant Pat. No. 26,801) in that 'DrisStrawNinetyOne' has medium leaf blistering, medium fruit glossiness, an outwards attitude of sepals on fruit, and a strong adherence of calyx on fruit, whereas 'DrisStrawFortyFour' has weak leaf blistering, strong fruit glossiness, an upwards attitude of sepals on fruit, and a very strong adherence of calyx on fruit.

'DrisStrawNinetyOne' differs from the reference variety 'DrisStrawFiftyThree' (U.S. Plant Pat. No. 29,749), in that 'DrisStrawNinetyOne' has a narrow width of band without achenes, a strong adherence of calyx on fruit, firm fruit, and absent or very small sized cavity in fruit, whereas 'DrisStrawFiftyThree' has a broad width of band without achenes on fruit, a very strong adherence of calyx on fruit, a medium firmness of fruit, and a medium sized cavity in fruit.

What is claimed is:

1. A new and distinct variety of strawberry plant named 'DrisStrawNinetyOne' as shown and described herein.

* * * * *